(12) United States Patent
Zaramella et al.

(10) Patent No.: US 9,845,293 B2
(45) Date of Patent: Dec. 19, 2017

(54) PROCESS FOR THE PREPARATION OF ESLICARBAZEPINE AND ESLICARBAZEPINE ACETATE

(71) Applicant: F.I.S.—FABBRICA ITALIANA SINTETICI S.P.A., Montecchio Maggiore (IT)

(72) Inventors: Simone Zaramella, Vigodarzere (IT); Emiliano Rossi, Padua (IT); Ottorino De Lucchi, Padua (IT); Siro Serafini, Vicenza (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 15/515,863

(22) PCT Filed: Feb. 23, 2016

(86) PCT No.: PCT/EP2016/053706
§ 371 (c)(1),
(2) Date: Mar. 30, 2017

(87) PCT Pub. No.: WO2016/142164
PCT Pub. Date: Sep. 15, 2016

(65) Prior Publication Data
US 2017/0305860 A1 Oct. 26, 2017

(30) Foreign Application Priority Data

Mar. 6, 2015 (IT) ............................ VI2015A0064
Nov. 19, 2015 (EP) ................................. 15195474

(51) Int. Cl.
*C07D 223/22* (2006.01)
*C07D 223/26* (2006.01)

(52) U.S. Cl.
CPC ...... *C07D 223/26* (2013.01); *B01J 2231/643* (2013.01); *B01J 2540/32* (2013.01)

(58) Field of Classification Search
CPC ..................................................... C07D 223/22
USPC ..................................................... 540/589
See application file for complete search history.

(56) References Cited

FOREIGN PATENT DOCUMENTS

| | | |
|---|---|---|
| EP | 2383261 A1 | 11/2011 |
| IN | 639/DEL/2011 | 1/2013 |
| WO | 9702250 A1 | 1/1997 |
| WO | 02092572 A1 | 11/2002 |
| WO | 2004031155 A1 | 4/2004 |
| WO | 2004087168 A1 | 10/2004 |
| WO | 2004099153 A1 | 11/2004 |
| WO | 2006005951 A1 | 1/2006 |
| WO | 2006056339 A1 | 6/2006 |
| WO | 2007012793 A1 | 2/2007 |
| WO | 2007117166 A1 | 10/2007 |
| WO | 2011045648 A2 | 4/2011 |
| WO | 2011091131 A2 | 7/2011 |
| WO | 2011117885 A1 | 9/2011 |
| WO | 2011131315 A1 | 10/2011 |
| WO | 2011138795 A2 | 11/2011 |
| WO | 2012026201 A1 | 3/2012 |
| WO | 2012121701 A1 | 9/2012 |
| WO | 2012156987 A2 | 11/2012 |
| WO | 2013008194 A2 | 1/2013 |

OTHER PUBLICATIONS

Parekh et al., "Ether-tethered Ru(u)/TsDPEN complexes; synthesis and applications to asymmetric transfer hydrogenation", Catalysis Science & Technology, 2012, vol. 2, No. 2, pp. 406-414.
International Search Report and Written Opinion for International Application No. PCT/EP2016/053706 (10 Pages) (Apr. 11, 2016).
"Process for the preparation of (10S)-10-hydroxy-10, 11-dihydro-5H-dibenzo[b,f]azepine-5-carboxamide", IP.com, 2010, 4 pages.

*Primary Examiner* — Brenda Coleman
(74) *Attorney, Agent, or Firm* — Lucas & Mercanti, LLP

(57) ABSTRACT

Object of the present invention is an improved process for the preparation of Elsicarbazepine and Eslicarbazepine acetate by means of chiral Ruthenium catalysts.

14 Claims, No Drawings

PROCESS FOR THE PREPARATION OF ESLICARBAZEPINE AND ESLICARBAZEPINE ACETATE

CROSS-REFERENCE TO RELATED APPLICATIONS

This application is a 371 of PCT/EP2016/053706, filed Feb. 23, 2016, which claims the benefit of Italian Application No. VI2015A000064, filed Mar. 6, 2015 and European Patent Application No. 15195474.0, filed Nov. 19, 2015.

TECHNICAL FIELD

The object of the present invention is an improved process for the synthesis of the pharmaceutically active substances known as Eslicarbazepine and Eslicarbazepine acetate.

BACKGROUND ART

Eslicarbazepine acetate is an anticonvulsant active pharmaceutical ingredient approved in Europe and in US for the treatment of epilepsy. Eslicarbazepine acetate is a pro-drug, indeed it deacetylates in vivo releasing the active substance Eslicarbazepine.

Eslicarbazepine is the main metabolite of Oxcarbazepine of formula (III):

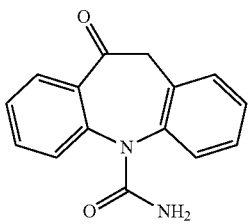

(III)

since, in vivo, Oxcarbazepine is reduced enantioselectively to Eslicarbazepine, by means of enzymes.

The chemical name of Eslicarbazepine acetate is (S)-10-Acetoxy-10,11-dihydro-5H-dibenz[b,f]azepine-5-carboxamide or 5H-Dibenz[b,f]azepine-5-carboxamide, 10-(acetyloxy)-10,11-dihydro-, (10S)- or (S)-(+)-Licarbazepine acetate and has formula (I):

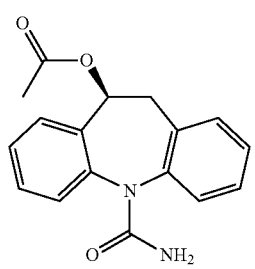

(I)

Eslicarbazepine is the (S) enantiomer of Licarbazepine, it gives optical rotation (+) and has the following formula (II):

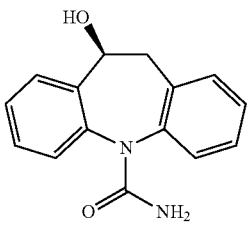

(II)

Finally, Licarbazepine is the racemic substance constituted of the two enantiomers (S)-(+)-Licarbazepine (Eslicarbazepine) and (R)-(−)-Licarbazepine, said Licarbazepine has therefore the following chemical formula:

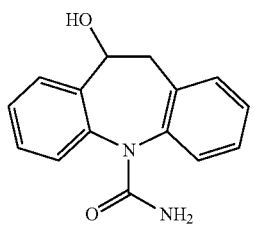 [SMILES: NC(=O)N1c2ccccc2CC(O)c2ccccc21]

In the publication WO9702250, Eslicarbazepine acetate is described for the first time. There are various known synthetic routes to Eslicarbazepine and Eslicarbazepine acetate based upon the following synthetic methods:

1. Resolution of Licarbazepine, including the classic optical resolution (chemical) or the enzymatic resolution, according to the following general scheme:

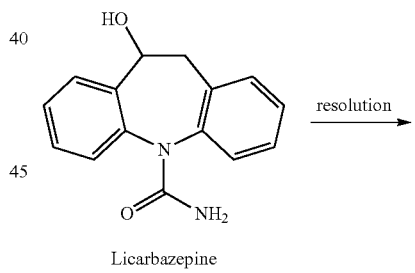

Licarbazepine

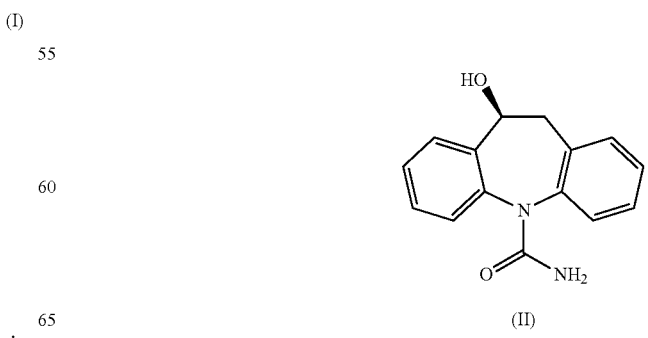

(II)

2. Chemical enantioselective reduction of Oxcarbazepine, according to the following general scheme:

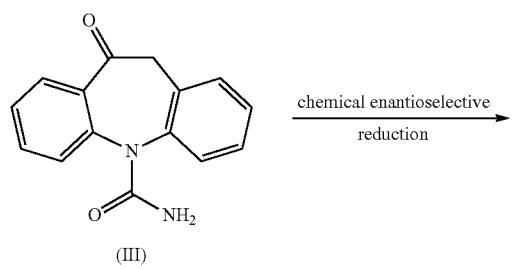

(III)

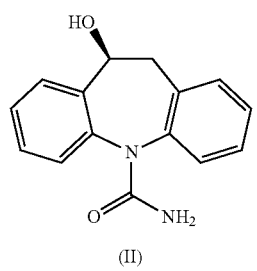

(II)

3. Enzymatic enantioselective reduction of Oxcarbazepine, according to the following general scheme:

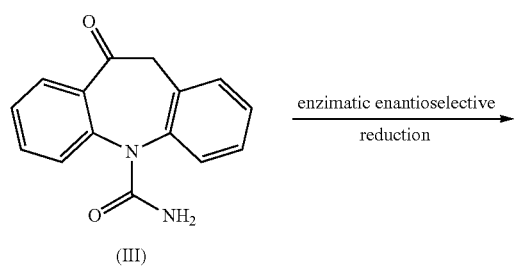

(III)

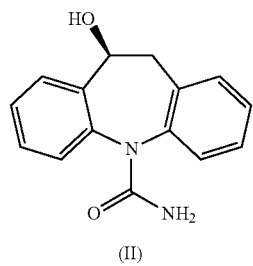

(II)

4. Chemical enantioselective reduction of Acetyloxcarbazepine, according to the following general scheme:

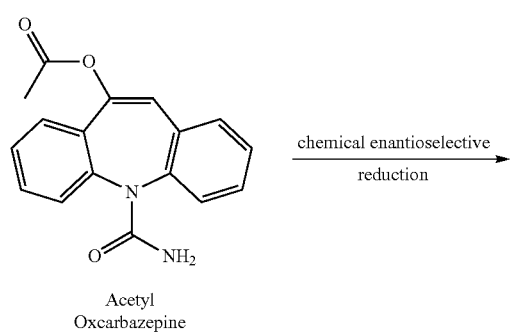

Acetyl Oxcarbazepine

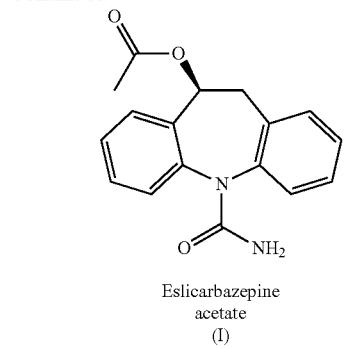

Eslicarbazepine acetate
(I)

In particular, the first synthetic route of Eslicarbazepine acetate can be generalized with the following scheme of synthesis starting from Oxcarbazepine (III):

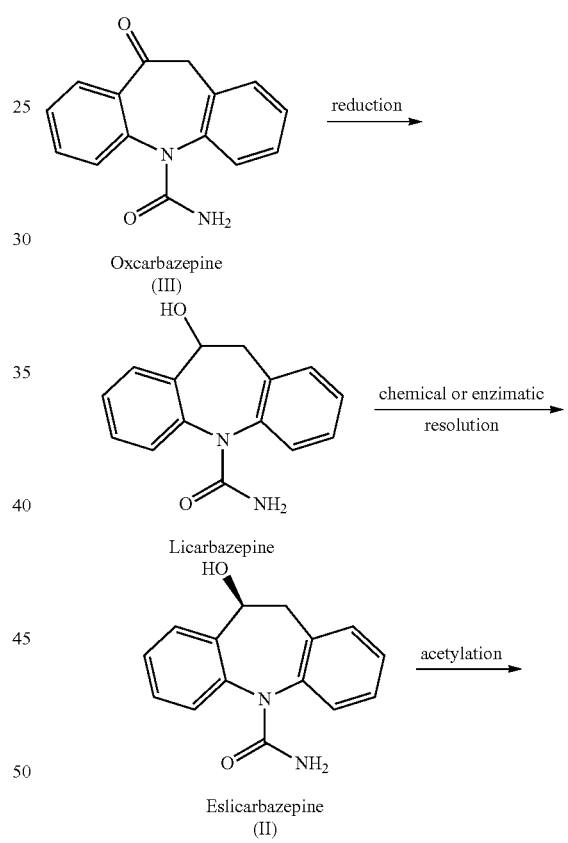

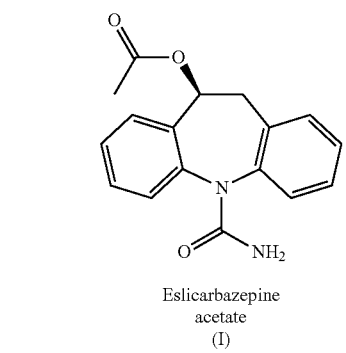

Eslicarbazepine acetate
(I)

This synthetic route is described for the first time in Journal of Medicinal Chemistry, Volume: 42, n. 14, Pages: 2582-2587, 1999, where Oxcarbazepine of formula (III):

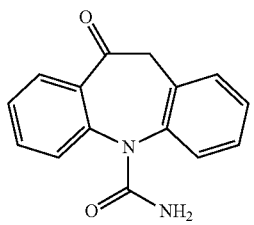

(III)

is reduced with sodium borohydride to give the racemic alcohol (Licarbazepine), which is then resolved via menthoxyacetate ester.

In the publication WO2002092572 the resolution of the racemic alcohol (Licarbazepine) is described via the corresponding esters of tartaric acid di-O, O'-substituted. Various esters are also specifically described.

Another procedure similar to that already described, but in which different chiral acids are employed, is reported in WO2011091131.

In WO2006056339 a method of chemical resolution is described, of the precursor of Licarbazepine in this case the nitrile intermediate.

The above synthetic routes for optical resolution are long (4 steps starting from Oxcarbazepine) and inefficient (more than half of the Oxcarbazepine is lost), even if subsequent publications (WO2004099153 and WO2006005951 and WO2013008194) describe also methods for the racemization or inversion of configuration of the other enantiomer (R).

The publication IN2009CH00220 describes an enzymatic process for the preparation of Eslicarbazepine acetate by means of the following steps: (a) dissolving the racemic Licarbazepine in a solvent; (b) adding an acylating agent and an enzyme; (c) only the (S)-Licarbazepine is acylated. Said method is based on the enzymatic resolution of acetyl Licarbazepine.

The document WO2011045648 describes an enzymatic resolution of racemic Licarbazepine methoxyacetylated. In one example the racemic Licarbazepine is methoxyacetylated, treated with liquid protease Protex 6 L, extracted, treated with succinic anhydride and then the ester is isolated and worked up to Eslicarbazepine acetate. This synthetic route appears long, laborious and not very efficient.

Another approach for the enzymatic resolution of Licarbazepine is that described in Tetrahedron, 68, (2012), 7613-7618.

In the literature, there are other documents relating to the resolution of racemic Licarbazepine.

In particular, in documents WO2011117885, WO2011138795, IN2011DE00639, WO2012121701, WO2012156987, WO2013008194, additional methods are described for the preparation of Eslicarbazepine by separation of different diasteromeric esters of Licarbazepine. Such esters are prepared by reaction of Licarbazepine with chiral acids and derivatives thereof.

The third approach for the synthesis of Eslicarbazepine is based on the enzymatic enantioselective reduction of Oxcarbazepine. This synthetic approach is efficient and consists of only two synthetic steps from Oxcarbazepine, as in the following scheme:

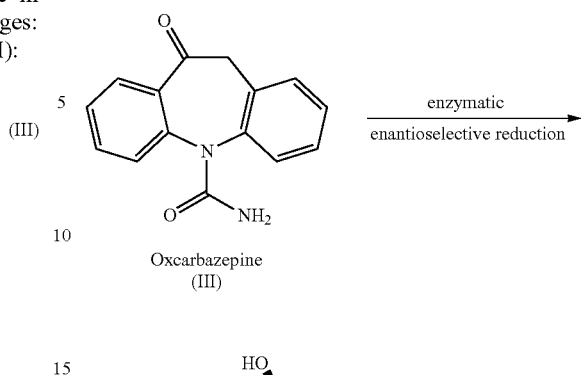

Oxcarbazepine (III)

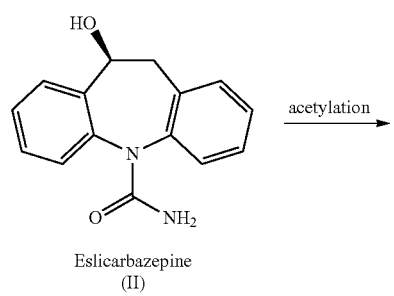

Eslicarbazepine (II)

acetylation

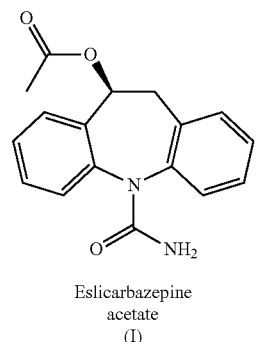

Eslicarbazepine acetate (I)

The publication IPCOM000193904D, dated 2010 March the 14th, discloses some results concerning the reduction of Oxcarbazepine to Eslicarbazepine with enzymes BioCatalytic (Codexis) KRED-114, 119, 130, 101 and enzymes BioCatalytic (Codexis) KRED-NADH-109, 108 and enzyme Enzysource ES-KRED-144. The conversions are low.

The fourth synthetic approach for the synthesis of Eslicarbazepine is through enantioselective reduction of acetyl Oxcarbazepine. This synthetic pathway can be summarized with the following scheme:

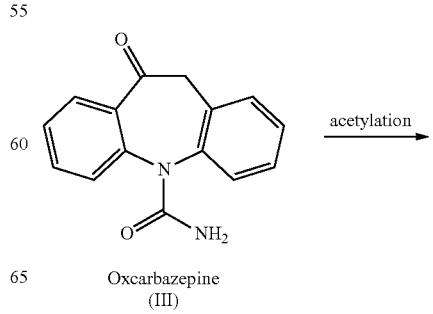

Oxcarbazepine (III)

acetylation

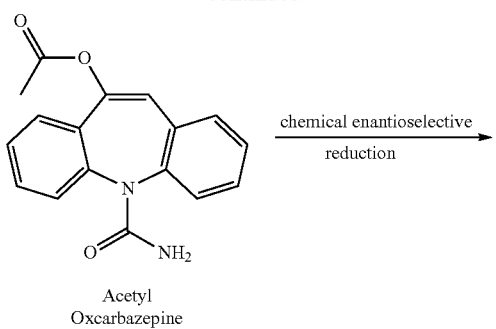

Acetyl
Oxcarbazepine

→ chemical enantioselective reduction →

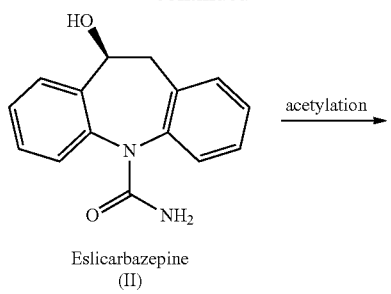

Eslicarbazepine
(II)

→ acetylation →

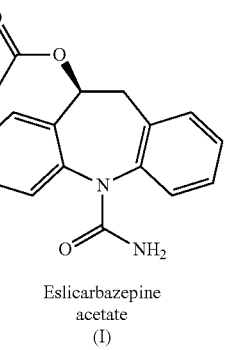

Eslicarbazepine
acetate
(I)

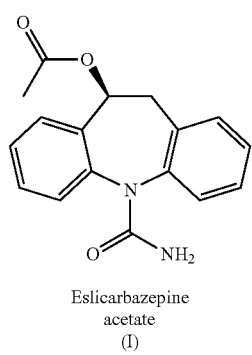

Eslicarbazepine
acetate
(I)

This synthetic approach is described for the first time in WO2007117166, wherein Eslicarbazepine acetate is directly prepared by asymmetric hydrogenation of 5H-Dibenz[b,f]azepine-5-carboxamide,10-(acetyloxy)-(compound obtained by acetylation of Oxcarbazepine) in the presence of a chiral catalyst and of a hydrogen source. For example the catalyst can be Rh(COD)(RcSp-DuanPhos)BF$_4$.

But, turning to the second synthetic approach for the preparation of Eslicarbazepine, namely the chemical enantioselective reduction of Oxcarbazepine, there is to be observed that this approach is much more interesting than the one described above for the resolution of the Licarbazepine as it is inherently more efficient (50% of the product is not wasted) and it involves few synthetic steps.

Said process can be generalized with the following scheme:

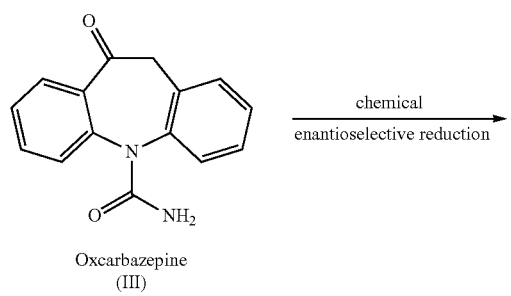

Oxcarbazepine
(III)

→ chemical enantioselective reduction →

An interesting publication concerning this second technology is the paper by Noyori, "Ruthenium (II)-Catalyzed Asymmetric Transfer Hydrogenation of Ketones Using a Formic Acid-Triethylamine Mixture", Journal of the American Chemical Society (1996), 118 (10), 2521-2, teaching of the which have been successfully applied to Eslicarbazepine synthesis, as described in WO2004031155.

The publication WO2004031155 describes an enantioselective "transfer hydrogenation" of Oxcarbazepine, by means of a catalytic system composed of a Ruthenium type metal and one of eight described ligands.

In particular, the examples 1, 2 and 3 of WO2004087168 describe the synthesis of Eslicarbazepine and its enantiomer by enantioselective reduction of Oxcarbazepine according to the following synthetic scheme:

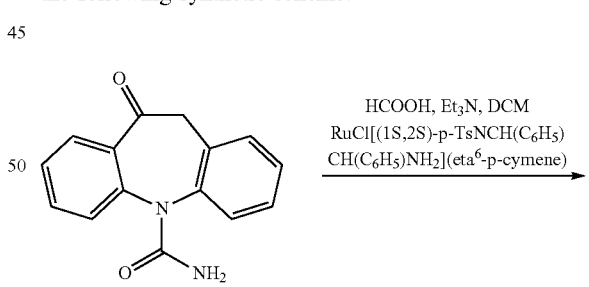

HCOOH, Et$_3$N, DCM
RuCl[(1S,2S)-p-TsNCH(C$_6$H$_5$)CH(C$_6$H$_5$)NH$_2$](eta$^6$-p-cymene)

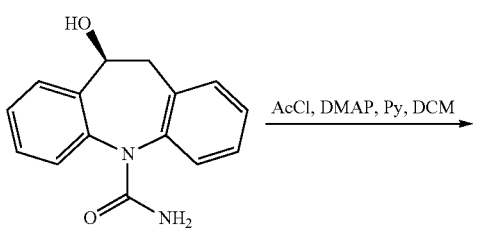

AcCl, DMAP, Py, DCM →

-continued

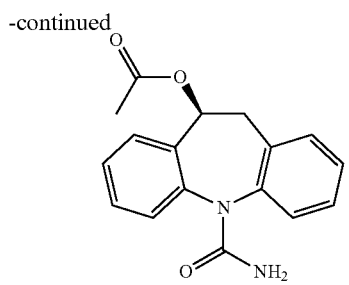

The chiral Ruthenium catalyst used to perform said enantioselective reduction which is, in particular, an asymmetric transfer hydrogenation, is the classical Noyori-type sulfonylated diamine ligands, a catalyst wherein the Rutenium atom is bounded coordinatively (only) to p-cymene ligand.

Unfortunately, said experiments do not disclose the amount of the product produced especially because the product is obtained after purification through flash chromatography and it is just reported that the product shows an e.e. >99%, the description does not discloses the yield neither.

Nevertheless this method shows some important drawbacks such as the need of purify the product through flash chromatography (both experiments 1 and 2) and a huge amount of chiral Ruthenuium catalyst is used, in particular, the molar ratio of the chiral Ruthenium catalyst to Oxcarbazepine of formula (III) is comprised in the range from 1:64 (example 2) to 1:100 (example 2 alternative). Said amount of catalyst, although by one side provides a very high effect in terms of e.e., to the other side it is not suitable for industrial productions, considering the high costs involved of the catalyst.

The PCT application WO2007012793, describes a process for the preparation of Eslicarbazepine via asymmetric reduction of Oxcarbazepine in the presence of a chiral catalyst and a hydrogen source, for example triethylammonium formate. The catalyst is a combination of [RuX2 (L)] 2, where L is a ligand (S, S) or (R, R) of formula:

I

Also in this case, in the catalyst for performing the enantioselective reduction of Oxacarbazepine to provide Eslicarbazepine the Rutenium atom is bounded coordinatively (only) to p-cymene ligand and the chiral ligand shows (S,S) configuration.

The example 1 of the PCT application WO2007012793, shows that said enantioselective reduction of Oxacarbazepine provides Eslicarbazepine with 95% of isolated molar yield, HPLC purity of 99.6% and 97.8% e.e., wherein the molar ratio of the ruthenium catalyst to Oxcarbazepine used is 1:4000.

In Example 2, Eslicarbazepine is produced with isolated molar yield of 94%, HPLC purity of 99.5%, 97.8% e.e., wherein the molar ratio of the ruthenium catalyst to Oxcarbazepine used is 1:2700.

In Example 4, Eslicarbazepine is produced with isolated molar yield of 88%, HPLC purity of 99.8%, 98.4% e.e., wherein the molar ratio of the ruthenium catalyst to Oxcarbazepine used is 1:5400.

The interesting results in terms of e.e. achieved by the process described in WO2007012793 are achieved controlling the pH of the reaction (see p. 4, l. 12-16), in particular carrying out the enantioselective reduction at pH comprised between 6.5 and 8.0 (see claim 1 and pag. 9 and 10).

In relation to the same technology, that is the enantioselective chemical reduction of Oxacarbazepine to give Eslicarbazepine, also the publication WO2011131315 and the related patent application EP2383261A1 are to be mentioned. In these publications a process of asymmetric reduction of Oxcarbazepine to produce Eslicarbazepine with ee greater than 85% is described, in which a catalyst enantiomerically enriched containing Ruthenium (in many examples a catalyst is described of the type RuX (L1) (L2)) or Rhodium) is used in the presence of a hydrogen donor (for example formic acid) and in the presence of an anionic ion exchange resin (for example IRA-67). It has been indeed found that the presence of said resin provides high conversions with good e.e. (see par. [0005] and claim 1 of EP2383261A1)

As in the previously described prior art documents, asymmetric reduction of Oxcarbazepine to produce Eslicarbazepine is carried in presence of a chiral catalytic catalyst wherein the Rutenium atom is bounded coordinatively (only) to p-cymene ligand and the chiral ligand of formula (I) shows (S,S) configuration.

In example 1 of EP2383261A1, said enetioselective reduction of Oxacarbazepine, in presence of IRA-67 and RuCl[(S,S)-Ts-DPEN](p-cymene), provides Eslicarbazepine with 74% of isolated molar yield, HPLC purity of 99.4% and 99.8% e.e., wherein the molar ratio of the chiral Ruthenium catalyst to Oxcarbazepine used is 1:1340.

In Example 2, Eslicarbazepine is produced in presence of IRA-67 and RuCl[(S,S)-Ts-DPEN](p-cymene) with isolated molar yield of 81%, HPLC purity of 98.8%, 98.1% e.e., wherein the molar ratio of the chiral Ruthenium catalyst to Oxcarbazepine used is 1:1160.

Differently from all the previous chiral Ruthenium catalysts described in WO2004031155 and WO2007012793, the document EP2383261A1 also describes a catalyst having the following general formula:

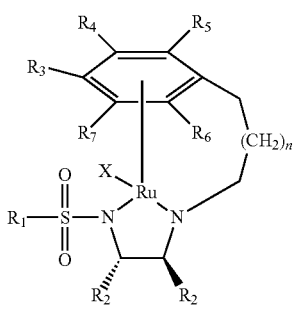

wherein the Rutenium atom is bounded to a ligand wherein the aryl ring (e.g. p-cymene) is covalently bounded to the chiral diamine ligand through a $(CH_2)_n$ bridge, and then the aryl group is bounded also coordinatively to the Ruthenium atom, as in the previous catalysts.

In particular, there is only one example where said new catalyst is specifically disclosed (named RuCl[(S,S)-teth- TsDPEN]) and used to carry out the enantioselective reduction of Oxcarbazepine to provide Eslicarbazepine being the second part of example 5 of EP2383261 (par. [0028]) were Eslicarbazepine was obtained, also in presence of IRA-67, with conversion of 83% (after 30 hours) and 86% e.e.

Moreover, the applicant states in par. [0029] that the enantiomeric purity of the product is lower when RuCl[(S,S)-teth-TsDPEN] is used instead of the Noyori-type catalyst RuCl[(S,S)-Ms-DPEN](p-cymene) or RuCl[(S,S)-Ts-DPEN](p-cymene).

From the previous prior art documents it is thus clear as a method for the preparation of Eslicarbazepine having an e.e. lower than 99.0%, typically around 98.0%, is the asymmetric reduction of Oxcarbezepine in presence of chiral Ruthenium catalysts having an aryl group bounded coordinatively, only, to the Ruthenium atom, and mandatorily operating at controlled pH, for example between 6.5 and 8.0, or carrying out the reduction in presence of an anionic ion exchange resin (for example IRA-67).

SUMMARY OF INVENTION

The problem addressed by the present invention is therefore that of providing an improved process for the preparation of Eslicarbazepine and then Eslicarbazepine acetate by means of an improved reaction of asymmetric reduction of Oxacarbazepine.

In particular, the problem of the present invention is to provide a better process for the preparation of Eslicarbazepine by asymmetric reduction of Oxcarbazepine, expecially in terms of both enantiomeric excess (e.e) and chemical purity.

This problem is solved by a process for the synthesis of Eslicarbazepine as outlined in the annexed claims, whose definitions are integral part of the present description.

Further features and advantages of the process according to the invention will result from the description hereafter reported of examples of realization of the invention, provided as an indication of the invention.

DESCRIPTION OF EMBODIMENTS

The present invention relates to a process for the preparation of Eslicarbazepine of formula (II):

(II)

by enantioselective reduction of Oxcarbazepine of formula (III):

(III)

characterized in that said enantioselective reduction is carried out in presence a chiral catalyst of formula (IV):

(IV)

wherein X is a hydrogen atom or a halogen atom,

R1 is selected between linear or branched $C_{1-5}$ alkyl, unsubstituted aryl, substituted aryl with a linear or branched $C_{1-5}$ alkyl group or is a linear or branched $C_{1-5}$ alkyl-aryl;

R2 is selected between hydrogen, linear or branched $C_{1-5}$ alkyl, linear or branched $C_{1-5}$ alkoxy group.

The catalyst of the invention differs from the previous used catalyst for preparing Eslicarbazepine, by enantioselective reduction of Oxcarbazepine, in that:

mainly, for the presence of the hydrogen atom bonded to the nitrogen atom bringing the alkoxy side chain; this hydrogen confers substantially another chiral center to the chiral catalyst and induces a conformational constraining of the skeleton of the ligand;

presence of oxygen atom in the side chain bringing the aromatic ring complexed with the Ruthenium atom.

Moreover, it should be observed that the aromatic ring complexed with the Ruthenium atom, is also covalently bonded to a nitrogen atom of the ligand, thus conferring rigidity to the conformation.

The necessary configuration S,S of the ligand for providing Eslicarbazepine, instead of the related enantiomer, was already known and established in WO2007012793.

It has been indeed surprisingly found that the enantioselective reduction of Oxcarbazepine in presence of the catalyst of the invention of formula (IV) is improved both in terms of enantioselectivity and chemical purity of the product Eslicarbazepine, keeping, at the same time:

low loading of the catalyst (since the catalyst of the invention shows high catalytic activity), high conversions/molar yields of the product Eslicarbazepine, and avoiding the purification with flash chromatography, avoiding the need of using anionic exchange resins and avoiding the need of working at controlled pH, in particular at pH comprised between 6.5 and 8.0.

The chiral catalyst of the invention, thus, allows the preparation of Eslicarbazepine through an improved enantioselective reduction of Oxcarbazepine, in particular, in terms of enantiomeric excess and, at the same time, chemical purity of the product.

Moreover, as secondary effect, it has been observed that the catalyst of the invention allows faster reaction rates of conversion of Oxcarbazepine to Eslicarbazepine when compared to the prior art catalysts.

Thus, the process of the invention allows the preparation of Eslicarbazepine with high chemical and optical purity, and it can also be carried out without controlling the pH in a range between 6.5 and 8.0 or in absence of anionic ion exchange resin, such as for example IRA-67, being said conditions the essentials one for the improvement processes of the prior art.

Moreover, the process of the invention is economically advantageous in terms of overall costs for unit of product, since the cost for the amount of the catalyst of formula (IV) to be used in the process is lower than the cost of the amounts of previous catalysts for unit of product.

In the chiral catalyst of formula (IV) of the process of the invention, the X substituent is a hydrogen atom or a halogen atom, i.e., can be hydrogen, fluorine, chlorine, bromine or iodine.

In the chiral catalyst of formula (IV) of the process of the invention, the linear or branched $C_{1-5}$ alkyl of R1 or, independently of R2, can be methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl.

The unsubstituted aryl group of R1 can be phenyl or naphthyl.

In the substituted aryl with a linear or branched $C_{1-5}$ alkyl group of R1, the substituent linear or branched $C_{1-5}$ alkyl group can be methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl; wherein the aryl group can be phenyl or naphtyl. Tosyl is a preferred R1 group.

In linear or branched $C_{1-5}$ alkyl-aryl of R1, the $C_{1-5}$ alkyl group is methylene, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl; wherein the aryl group can be phenyl or naphtyl.

The linear or branched $C_{1-5}$ alkoxy group of R2 can be methoxy, ethoxy, n-propoxy, isopropoxy, n-butoxy, sec-butoxy, n-pentoxy, etc.

According to a preferred embodiment of the invention, in the chiral catalyst of formula (IV) of the process of the invention, X is chlorine.

According to a preferred embodiment of the invention, in the chiral catalyst of formula (IV) of the process of the invention, R2 is methyl.

According to a more preferred embodiment of the invention, in the chiral catalyst of formula (IV) of the process of the invention, X is chlorine and R2 is methyl.

According to a preferred embodiment of the invention, in the chiral catalyst of formula (IV) of the process, R1 is methyl or tosyl.

According to a more preferred embodiment of the invention, in the chiral catalyst of formula (IV) of the process of the invention, X is chlorine and R2 is methyl and R1 is methyl or tosyl.

Thus, according to a more preferred embodiment, the chiral catalyst of formula (IV) is (S,S)-Ts-DENEB™ or (S,S)-Ms-DENEB™ having respectively the following chemical structure:

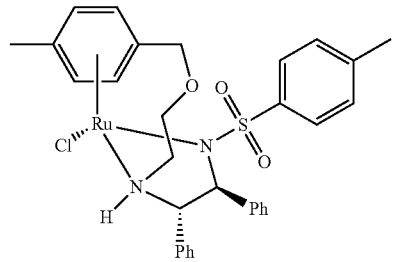

(S,S)-Ts-DENEB

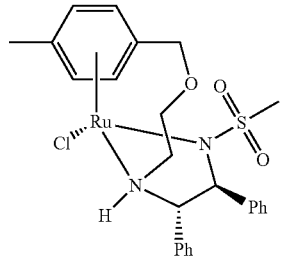

(S,S)-Ms-DENEB

The chiral catalyst (S,S)-Ts-DENEB, indexed with CAS RN [1384974-37-1] and CAS chemical name Ruthenium, chloro[4-methyl-N-[(1S,2S)-2-[(R)-[2-[[(1,2,3,4,5,6-η)-4methylphenyl]methoxy]ethyl]amino-κN]-1,2-diphenylethyl]benzenesufonamidato-κN]-, stereoisomer; can be purchased by Takasago International Corporation (Japan) or can be prepared according to the teaching of WO2012/026201, example 7 or 39 (but preparing instead the S,S enantiomer). The chiral catalyst (S,S)-Ts-DENEB is also sometimes named RuCl-(S,S)-Ts-DENEB.

The chiral catalyst (S,S)-Ms-DENEB, having a methyl group instead of the tosyl group as R1 substituent, can be purchased by Takasago International Corporation (Japan) or can be prepared according to the teaching of WO2012/026201, example 9. The chiral catalyst (S,S)-Ms-DENEB is also sometimes named RuCl-(S,S)-Ms-DENEB.

According to another preferred embodiment of the invention, in the process, the molar ratio of the chiral Ruthenium catalyst to Oxcarbazepine of formula (III) is comprised in the range from 1:200 to 1:1000.

According to more preferred embodiment of the invention, in the process, the molar ratio of the chiral Ruthenium catalyst to Oxcarbazepine of formula (III) is comprised in the range from 1:250 to 1:500, more preferably is about 1:400.

The enantioselective reduction can be a asymmetric transfer hydrogenation or an hydrogenation reaction.

According to another preferred embodiment of the invention, the enantioselective reduction is asymmetric transfer hydrogenation.

For carrying out the asymmetric transfer hydrogenation the hydride source can be formic acid, 1,4-diazabicyclo[2.2.2]octane, an alkali metal, alkylammonium salt of formic acid, or 2-propanol and a tertiary amine, such as for example triethylamine, diisopropylamine, tributylamine, etc.

According to a preferred embodiment of the invention, formic acid with triethylamine or 1,4-diazabicyclo[2.2.2] octane with triethylamine are the preferred hydride source since they provide the better, excellent, purity profile.

According to an again more preferred embodiment of the invention, the hydride source is formic acid and triethylamine.

According to a more preferred embodiment of the invention, the mixture of formic acid (3.6 eq.) with triethylamine (1.4 eq.) or the mixture 1,4-diazabicyclo[2.2.2]octane (3.6 eq.) with triethylamine (1.4 eq.) work comparably and provide excellent purity profile.

The enantioselective reduction can be carried out in an organic solvent, such as, an alcohol, an ether or an hydrocarbon solvent.

According to a preferred embodiment of the invention, the enantioselective reduction is carried out in methanol or tetrahydrofuran, since they provides the better results.

According to a preferred embodiment, the enantioselective reduction is an asymmetric transfer hydrogenation that can be carried out in an organic solvent, such as, an alcohol, an ether or an hydrocarbon solvent, more preferably, asymmetric transfer hydrogenation can be carried out in methanol or tetrahydrofuran.

According to a preferred embodiment of the invention, the enantioselective reduction is carried out at a temperature comprised between 50° C. and 80° C., more preferably at about 60° C.

According to a preferred embodiment of the invention, the enantioselective reduction is carried out at a pH of 9.0 to 12.0, more preferably between 10.5 and 11.0.

According to a preferred embodiment of the invention, the process of the invention also comprises the further step of conversion of Eslicarbazepine of formula (II) to give Eslicarbazepine acetate of formula (I).

Thus, further object of the invention is a process for the preparation of Eslicarbazepine acetate of formula (I):

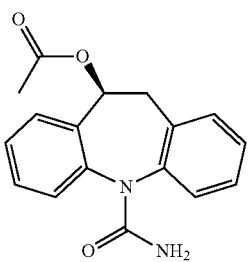

(I)

comprising the following steps:
A. preparation of Eslicarbazepine of formula (II):

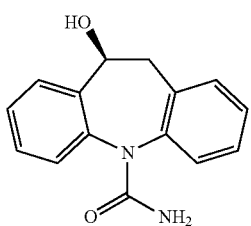

(II)

according to the process above described,

B. conversion of Eslicarbazepine of formula (II) as prepared in step A to give Eslicarbazepine acetate of formula (I).

The step B of conversion of Eslicarbazepine of formula (II) as prepared in step A to give Eslicarbazepine acetate of formula (I) can be carried out in many ways: by acetylation reaction, transacetylation reaction, enzymatic reaction or Mitsunobu reaction, etc.

The transacetylation reaction can be carried out using a proper catalyst and ethyl acetate, tryfluoroethyl acetate, vinylacetate or 2-propenylacetate.

The enzymatic reaction for converting Eslicarbazepine to Eslicarbazepine acetate can be carried out with vinyl acetate and a lipase.

The Mitsunobu reaction can be carried out with an alcohol, acetic acid, diethylazodicarboxylate, diisopropylazodicarboxylate preferably in presence of chiral alcohol.

According to a preferred embodiment of both the processes, the conversion of Eslicarbazepine of formula (II) to give Eslicarbazepine acetate of formula (I) is carried out by acetylation reaction.

The acetylation reaction can be conveniently carried out by means of an acetylating reagent such as for example acetic anhydride, acetyl halide such as acetyl chloride or bromide, trimethylortoacetate, triethylortoacetate, etc.

According to a preferred embodiment, the acetylation reaction can be conveniently performed in presence of a base, for example, triethylamine.

According to a preferred embodiment, the acetylation reaction can be conveniently performed in presence of a catalyst, for example, dimethylaminopyridine (DIMAP).

According to the process of the present invention, the step B of Eslicarbazepine acetylation, can be conveniently carried out by means of procedures known in the prior art, which include acetylation with acetic anhydride or acetyl chloride or bromide, optionally in the presence of a base.

According to a preferred embodiment of the process for preparing Eslicarbazepine acetate, Eslicarbazepine of formula (II) is isolated and then acetylated to produce Eslicarbazepine acetate of formula (I).

Thus, an object of the invention is also the use of Eslicarbazepine of formula (II) prepared according to the process of the invention for the preparation of Eslicarbazepine acetate of formula (I).

The chiral catalyst of formula (IV):

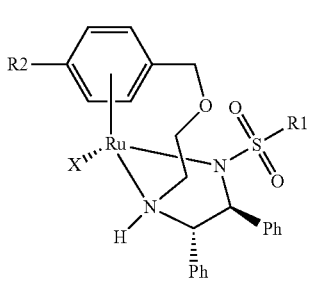

(IV)

wherein X is a hydrogen atom or a halogen atom,
R1 is selected between linear or branched $C_{1-5}$ alkyl, unsubstituted aryl, substituted aryl with a linear or branched $C_{1-5}$ alkyl group or is a linear or branched $C_{1-5}$ alkyl-aryl;
R2 is selected between hydrogen, linear or branched $C_{1-5}$ alkyl, linear or branched $C_{1-5}$ alkoxy group; wherein the meanings of X and R1 and R2 are the same of those given above, can be thus used for the preparation of Eslicarbazepine of formula (II) or Eslicarbazepine acetate of formula (I).

According to a preferred embodiment, is preferred the use of the chiral Ruthenium catalyst of formula (IV) being (S,S)-Ts-DENEB™ or (S,S)-Ms-DENEB™ for the preparation of Eslicarbazepine of formula (II) or Eslicarbazepine acetate of formula (I).

Another object of the invention are pharmaceutical compositions comprising Eslicarbazepine acetate of formula (I) prepared according to the process of the invention and one or more pharmaceutically acceptable excipients.

Another object of the invention is Eslicarbazepine acetate of formula (I) prepared according to the process of the invention or pharmaceutical compositions comprising said substance prepared according to the process of the invention for use in medicine.

Another object of the invention is Eslicarbazepine acetate of formula (I) prepared according to the process of the invention or pharmaceutical compositions comprising said substance prepared according to the process of the invention for use as anticonvulsant.

Finally, the process of the invention is a very cost-effective process.

A further study of development of the process of the invention has been carried out, especially directed to reduce again the amount of the catalyst to exploit at best the process of the invention by an economical point of view, which means producing Eslicarbazepine and then Eslicarbazepine acetate at the lowest possible cost.

To said aim, the parameter concerning the amount of catalyst has been further investigated, in particular, at the lower part of the range.

It has been thus found that the process of the invention performs well also using lower amounts of catalyst of formula (IV), indeed the process of the invention works also when the molar ratio of the chiral Ruthenium catalyst of formula (IV) to Oxcarbazepine of formula (III) is 1:3330, i.e. when 0.0003 molar equivalents of catalyst of formula (IV) to Oxcarbazepine of formula (III) are used.

Thus, according to another preferred embodiment of the invention, in the process, the molar ratio of the chiral Ruthenium catalyst of formula (IV) to Oxcarbazepine of formula (III) is comprised in the range from 1:200 to 1:3330, i.e. from 0.005 to 0.0003 molar equivalents of catalyst of formula (IV) to Oxcarbazepine of formula (III).

According to more preferred embodiment of the invention, in the process, the molar ratio of the chiral Ruthenium catalyst of formula (IV) to Oxcarbazepine of formula (III) is comprised in the range from 1:1000 to 1:3330, i.e. from 0.001 to 0.0003 molar equivalents of catalyst of formula (IV) to Oxcarbazepine of formula (III).

According to an again more preferred embodiment of the invention, in the process, the molar ratio of the chiral Ruthenium catalyst of formula (IV) to Oxcarbazepine of formula (III) is comprised in the range from 1:1430 to 1:3330, i.e. from 0.0007 to 0.0003 molar equivalents of catalyst of formula (IV) to Oxcarbazepine of formula (III).

According to an again more preferred embodiment of the invention, in the process, the molar ratio of the chiral Ruthenium catalyst of formula (IV) to Oxcarbazepine of formula (III) is 1:2000, i.e. 0.0005 molar equivalents of catalyst of formula (IV) to Oxcarbazepine of formula (III).

The enantioselective reduction can be carried out in an organic solvent, such as, an alcohol, an ether, an hydrocarbon solvent, nitrile solvent, or DMF (dimethylformamide) or NMP (N-Methyl-2-pyrrolidone).

The alcohol solvent can be, e.g., methanol, ethanol, isopropanol, etc.

The nitrile solvent can be, e.g., acetonitrile.

According to a preferred embodiment of the invention, the enantioselective reduction is carried out in methanol or tetrahydrofuran, since they provides the better results.

According to a preferred embodiment, the enantioselective reduction is an asymmetric transfer hydrogenation that can be carried out in an organic solvent, such as, an alcohol, an ether, an hydrocarbon solvent, nitrile solvent, or DMF or NMP, more preferably, asymmetric transfer hydrogenation can be carried out in methanol or tetrahydrofuran.

According to another preferred embodiment of the invention, the enantioselective reduction is carried out with a range of pH comprised between 4.5 and 7.5, preferably between 5.7 and 6.3.

EXPERIMENTAL SECTION

The starting material Oxcarbazepine is a substance commercially available, for example, provided by Sigma-Aldrich Inc. (USA).

Example 1: Synthesis of Eslicarbazepine

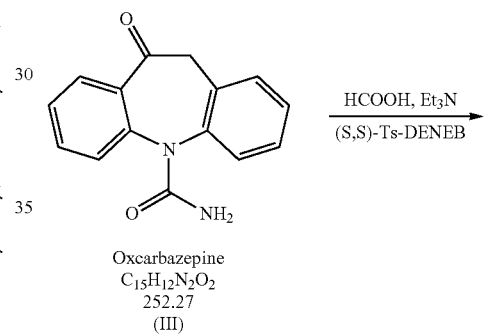

Oxcarbazepine
$C_{15}H_{12}N_2O_2$
252.27
(III)

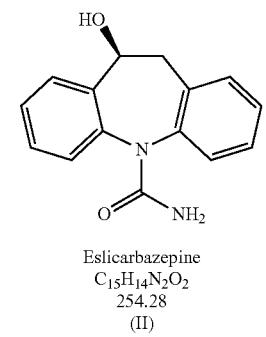

Eslicarbazepine
$C_{15}H_{14}N_2O_2$
254.28
(II)

In a 100 ml glass vessel, Oxcarbazepine was charged (10 g, 40 mmol) followed by 100 ml of THF. To the stirred suspension of Ruthenium chiral catalyst (S,S)-Ts-DENEB (0.005 eq, 129 mg, 0.198 mmol) was added under nitrogen atmosphere, followed by a mixture of formic acid (3.5 eq, 5.3 ml, 140 mmol) and triethylamine (1.45 eq, 8 ml, 57 mmol). The resulting mixture was heated under stirring to reflux temperature and maintained for approximately 16 hours, during which dissolution occurred. After cooling to 50° C., decolorizing charcoal (0.5 g) was added to the solution, stirred for 30 minutes then filtered over dicalite pad; some THF was used for rinsing. The resulting solution was allowed to cool to 40° C., then extracted twice at this temperature with 25 ml of saturated NaCl aqueous solution. The organic layer was then concentrated under vacuum to small volume (approximately 30 ml) and following 30 ml MTBE were added dropwise. The resulting suspension was stirred at room temperature for 40 minutes, then filtered and washed with 15 ml of MTBE. The product was dried under vacuum at 40° C. for 3 hours to afford an off-white powder: 79% isolated yield (8 g) of Eslicarbazepine. HPLC (A/A %): 99.7% product, 98.7% e.e., 0.1% Oxcarbazepine.

Example 2: Synthesis of Eslicarbazepine

In a 100 ml glass vessel, Oxcarbazepine was charged (10 g, 40 mmol) followed by 100 ml of methanol. To the stirred suspension of Ruthenium chiral catalyst (S,S)-Ts-DENEB (0.005 eq, 130 mg, 0.200 mmol) was added under nitrogen atmosphere, followed by a mixture of formic acid (3.5 eq, 5.3 ml, 140 mmol) and triethylamine (1.45 eq, 8 ml, 57 mmol). The mixture was heated under stirring to reflux temperature for 4 hours. After cooling to 50° C., decolorizing charcoal (0.5 g) was added to the mixture, stirred for 30 minutes then filtered over dicalite pad; some methanol was used for rinsing. The resulting solution was concentrated under vacuum to a final volume of approximately 50 ml. Upon cooling to 0° C. the product precipitated. Water (20 ml) was added and the suspension stirred at 0° C. for 1 hour, then filtered and washed with 15 ml of a methanol/water mixture (1:2). The product was dried under vacuum at 40° C. for 8 hours to afford an off-white powder: 66% isolated yield (6.7 g) of Eslicarbazepine. HPLC (A/A %): 100% product, 98.6% e.e.

Example 3: Synthesis of Eslicarbazepine

In a 100 ml glass vessel, Oxcarbazepine (10 g, 40 mmol), of Ruthenium chiral catalyst (S,S)-Ts-DENEB (0.0025 eq, 65 mg, 0.100 mmol) and methanol (50 ml) were charged. The suspension was stirred under nitrogen atmosphere at room temperature for 10 minutes, following a mixture of formic acid (3.5 eq, 5.3 ml, 140 mmol) and triethylamine (1.45 eq, 8 ml, 57 mmol) was added. The mixture was heated under stirring to reflux temperature for 8 hours. After cooling to 50° C., decolorizing charcoal (0.5 g) was added to the mixture, stirred for 30 minutes then filtered over dicalite pad; some methanol was used for rinsing. The resulting solution was concentrated under vacuum to approximately half volume. The solution was heated to 45° C. and 40 ml water were slowly added. The clear solution was then cooled slowly to 0° C. and stirred at this temperature for 30 minutes. The resulting product slurry was filtered and washed with 15 ml of a methanol/water mixture (1:2). The product was dried under vacuum at 40° C. for 8 hours to afford an off-white powder: 76% isolated yield (7.7 g) of Eslicarbazepine. HPLC (A/A %): 100% product, 98.7% e.e.

Example 4: Synthesis of Eslicarbazepine Acetate

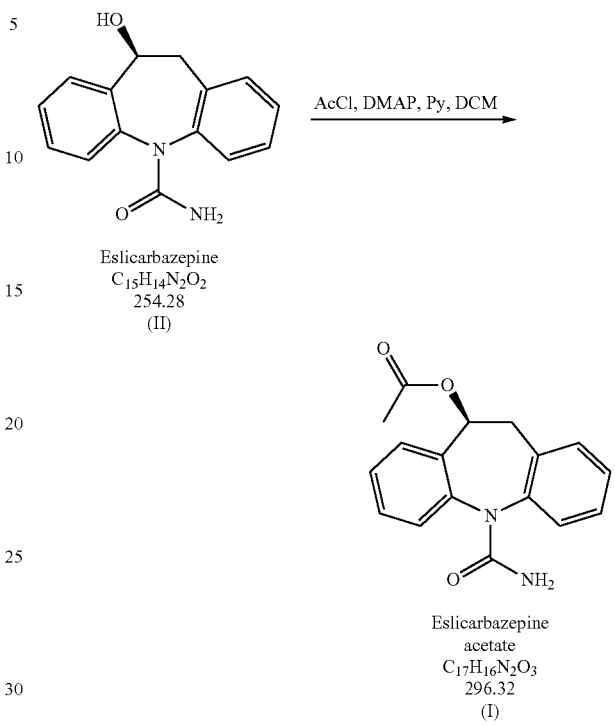

(10S)-10-hydroxy-10,11-dihydro-5H-dibenzo[b,f]azepine-5-carboxamide (Eslicarbazepine, 5 g, 20 mmol), as prepared in example 3, and 4-dimethylaminopyridine (DMAP, 0.05 g, 0.4 mmol) were charged in a 100 ml glass vessel and suspended in dichloromethane (25 ml). Triethylamine (1.2 eq, 3.3 ml, 24 mmol) was added and the mixture cooled to 0/5° C. Acetic anhydride (1.2 eq, 2.4 g, 24 mmol) was added dropwise and following the mixture was heated to reflux temperature (40° C.) resulting in complete dissolution. After 1 hour stirring solution was cooled to 5/10° C. and quenched by addition of aqueous hydrochloric acid solution (5% by weight, 25 ml). Biphasic mixture was allowed to warm up to room temperature, phases were separated and the organic layer was washed with aqueous sodium bicarbonate solution (5% by weight, 20 ml) and following with water (20 ml, then concentrated under vacuum to residue. To the solid were added dichloromethane (5 ml) and ethyl acetate (25 ml) and the resulting suspension was stirred at 40° C. for 15 minutes, then cooled to 0/5° C. and stirred at this temperature for 30 minutes. The resulting product slurry was filtered and washed with 5 ml of chilled ethyl acetate. The product was dried under vacuum at 40° C. for 8 hours to afford an off-white powder: 80% isolated yield (4.7 g) of Eslicarbazepine acetate. HPLC (A/A %): 100% product, 99.8% e.e.

Example 5: Analytical Methods

Chromatographic Conditions:
Chemical purity of both Eslicarbazepine and Eslicarbazepine acetate was determined using an Xbridge 100*4.6*3.5 mm column, mobile phase A=0.1% $HClO_4$, mobile phase B=Acetonitrile, 1.0 ml/min, 25° C., UV 210 nm.

Chiral purity of Eslicarbazepine was determined using an AD-H Chiral pak 250*4.6*5 mm column, mobile phase n-Heptane/Ethanol 75/25, 1.0 ml/min, 40° C., UV 210 nm.

Chiral purity of Eslicarbazepine acetate was determined using an AD-H Chiral pak 250*4.6*5 mm column, mobile phase n-Heptane/Ethanol 85/15, 1.5 ml/min, 40° C., UV 210 nm.

Example 6: Preparation of Eslicarbazepine—Comparative Examples

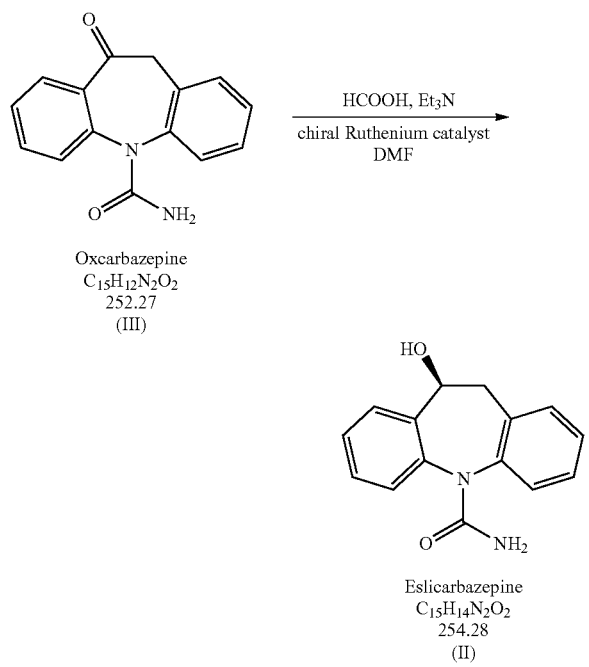

Four experiments have been carried out keeping constant the substrate concentration, temperature, hydrogen donor system and amount, catalyst loading, and solvent according to the conditions of the table below, as well as any other parameter/variable, except the kind of catalyst. Because of the poor solubility of Oxcarbazepine in most typical process solvents, DMF was chosen for the screening, since it enables to operate in homogeneous conditions at relatively high substrate concentrations.

| Conditions | | | | |
|---|---|---|---|---|
| Catalyst eq | DMF vol | Reaction T | Formic acid eq. | Triethylamine eq. |
| 0.005 eq | 10 vol | 75° C. | 3.6 eq | 1.4 eq |

| Catalysts | | | | |
|---|---|---|---|---|
| Catalyst | Supplier | CAS # | M.W. | Code name |
| RuCl[(S,S)-Ts-DPEN] (mesitylene) | Aldrich | 174813-81-1 | 622.18 | CAT.1 |
| RuCl[(S,S)-Fs-DPEN] (p-cymene) | Aldrich | 1026995-72-1 | 712.14 | CAT.2 |
| RuCl[(S,S)-Ts-DPEN] (p-cymene) | Aldrich | 192139-90-5 | 636.22 | CAT.3 |
| (S,S)-Ts-DENEB | Takasago | 1384974-37-1 | 650.19 | CAT.4 |

All 4 catalysts are commercially available (see supplier column).

Experimental Set-Up

Reaction vessel: 25-mL test tube (EasyMax) with screw cap, septum, magnetic stir bar, temperature probe.

Reaction scale: 1 g of Oxcarbazepine.

Materials: Oxcarbazepine Rixx A1500049.

Raw materials input: all charges are made on physical basis (vs. Oxcarbazepine).

Procedure

Oxcarbazepine (1 g) is charged in the vessel, followed by DMF (5 mL). The mixture is stirred until the solid is uniformly distributed. The catalyst is added and the catalyst vial is rinsed several time with a total of 5 mL of DMF. A mixture of formic acid (533 µL) and triethylamine (800 µL) is added. The mixture is heated to 75° C. (a clear solution is obtained). The reaction mixture is sampled after 2, 4, 6, 12, 24 h. The solution is analysed by HPLC for conversion and chiral purity.

Comments

The results of the experiments are reported in Table 1, Table 2, and Table 3. The main outcome and observations of the test are:

- All four catalysts effectively mediated the synthesis of Eslicarbazepine with good conversion and enantiomeric excess.
- Conversions >99% were obtained with CAT.2 (after 12 h) and CAT.4 (i.e. (S,S)-Ts-DENEB) (after 6 h, only). The other two catalysts did not lead to complete conversion at 24 h and the reaction appeared to stall. Addition of extra formic acid/triethylamine as kicker charge provided only a modest boost to the reaction.
- The impurity profile of CAT.1 and CAT.3 had a much higher impurity load with time (12.6-15 LCAP after 24 h). In particular, the impurity at rrt 2.28-2.33 grew constantly with time, reaching as high as 10.2-11.5 LCAP at 24 h. The impurity is suspected to be Oxodihydroiminostilbene.
- Chiral purity with ee >98% was obtained with CAT.2 and CAT.4. The ee did not depend on the reaction progression.
- CAT.4 (i.e. (S,S)-Ts-DENEB) provides the best results in terms of both HPLC purity and e.e. (see table 1 and, especially Table 2 provide evidence).
- CAT.4 (i.e. (S,S)-Ts-DENEB) provides the best selective reaction and cleanest reaction (See Table 2).
- The pH of reaction streams was 10.5-11.0 throughout the reaction course.
- All solvents and reagents were used as such, no degassing procedures were applied. No precaution for excluding air/oxygen from the vessel was taken.

TABLE 1

Comparison of Ru catalysts, with same loading of 0.005 eq.

| Exp # | Age time [h] | Conversion | Total imp. LCAP | ee % |
|---|---|---|---|---|
| RD/0008 | 2 | 77.1% | 1.22 | 96.9% |
| RuCl[(S,S)-Ts-DPEN](mesitylene) | 4 | 81.6% | 3.95 | 96.9% |
| | 6 | 84.0% | 5.89 | 96.7% |
| | 12 | 91.3% | 10.31 | 97.0% |
| | 24 | 95.9% | 15.05 | 96.8% |
| | 26 | 96.7% | 15.69 | 96.8% |
| RD/0009 | 2 | 74.9% | 0.00 | 98.2% |
| RuCl[(S,S)-Fs-DPEN](p-cymene) | 4 | 93.0% | 0.38 | 98.2% |
| | 6 | 96.2% | 0.65 | 98.1% |
| | 12 | 99.0% | 0.86 | 98.2% |
| | 24 | 99.7% | 1.58 | 98.0% |
| RD/0010 | 2 | 80.3% | 1.67 | 97.7% |
| RuCl[(S,S)-Ts-DPEN](p-cymene) | 4 | 83.4% | 4.14 | 97.5% |
| | 6 | 86.1% | 5.99 | 97.6% |
| | 12 | 93.2% | 9.48 | 97.8% |
| | 24 | 96.4% | 12.62 | 97.6% |
| | 26 | 98.5% | 12.10 | 97.5% |
| RD/0013 | 2 | 97.5% | 2.53 | 98.4% |
| [(S,S)-Ts-DENEB] | 4 | 97.7% | 10.37 | 99.3% |
| | 6 | 100% | 9.06 | 99.3% |
| | 12 | 100% | 0.85 | 98.4% |
| | 24 | 100% | 0.00 | 98.3% |

(*) Age time at 26 h corresponds to addition of 25% extra formic acid/triethylamine.

TABLE 2

Impurity profile of Eslicarbazepine synthesis, In Process Control analysis (IPCs)

| | | HPLC LCAP | | | | | | | | |
|---|---|---|---|---|---|---|---|---|---|---|
| Exp # | Age time [h] | Eslicarbaze RRT 1.00 | Imp. RRT 1.07 | Imp. RRT 1.17 | Oxcarbazepine RRT 1.45 | Imp. RRT 1.76 | Imp. RRT 1.98 | Imp. RRT 2.02 | Imp. RRT 2.28-2.33 | Imp. RRT 3.38-3.40 |
| RD/0008 | 2 | 76.18 | — | — | 22.60 | — | — | — | 1.22 | — |
| | 4 | 78.35 | — | — | 17.70 | — | — | — | 3.95 | — |
| | 6 | 79.06 | — | — | 15.05 | — | — | — | 5.89 | — |
| | 12 | 81.91 | — | 1.38 | 7.78 | 0.84 | — | — | 8.09 | — |
| | 24 | 81.47 | — | 1.68 | 3.48 | 1.86 | — | — | 11.50 | — |
| | 26 | 81.56 | — | 1.86 | 2.75 | — | 1.36 | 1.42 | 11.04 | — |
| RD/0009 | 2 | 74.88 | — | — | 25.12 | — | — | — | — | — |
| | 4 | 92.60 | — | — | 7.02 | — | — | — | 0.38 | — |
| | 6 | 95.55 | — | — | 3.80 | — | — | — | 0.66 | — |
| | 12 | 98.17 | 0.85 | — | 0.97 | — | — | — | — | — |
| | 24 | 98.13 | — | — | 0.29 | — | — | 0.46 | 1.12 | — |
| RD/0010 | 2 | 78.97 | — | — | 19.36 | — | — | — | 1.65 | — |
| | 4 | 79.98 | — | — | 15.88 | — | — | — | 4.14 | — |
| | 6 | 80.95 | — | — | 13.06 | — | — | — | 5.99 | — |
| | 12 | 84.38 | — | 1.09 | 6.14 | 0.66 | — | — | 7.73 | — |
| | 24 | 84.24 | — | 1.18 | 3.14 | 1.26 | — | — | 10.18 | — |
| | 26 | 86.61 | — | — | 1.29 | — | 1.65 | 0.90 | 9.55 | — |
| RD/0013 | 2 | 96.59 | — | — | 2.50 | — | — | — | — | 0.90 |
| | 4 | 97.55 | — | — | 2.22 | — | — | — | — | 0.23 |
| | 6 | 99.60 | — | — | 0.00 | — | — | — | — | 0.40 |
| | 12 | 99.34 | — | — | 0.00 | — | — | — | — | 0.66 |
| | 24 | 99.35 | — | — | 0.00 | — | — | — | — | 0.65 |

(*) Age time at 26 h corresponds to addition of 25% extra formic acid/triethylamine.

TABLE 3

Impurity profile of Eslicarbazepine synthesis, chiral IPCs

| | | HPLC LCAP | | |
|---|---|---|---|---|
| Exp # | Age time [h] | R-Licarbazepine RRT 0.59 | Eslicarbazepine RRT 1.00 | Oxcarbazepine RRT 1.09 |
| RD/0008 | 2 | 1.23 | 77.88 | 20.88 |
| | 4 | 1.31 | 81.89 | 16.80 |
| | 6 | 1.41 | 84.09 | 14.50 |
| | 12 | 1.39 | 90.16 | 8.45 |
| | 24 | 1.56 | 95.54 | 2.90 |
| | 26 | 1.55 | 95.01 | 3.44 |
| RD/0009 | 2 | 0.67 | 74.64 | 24.69 |
| | 4 | 0.83 | 92.85 | 6.32 |
| | 6 | 0.92 | 96.18 | 2.90 |
| | 12 | 0.88 | 98.22 | 0.90 |
| | 24 | 0.99 | 98.79 | 0.22 |
| RD/0010 | 2 | 0.96 | 81.00 | 18.04 |
| | 4 | 1.05 | 83.91 | 15.04 |
| | 6 | 1.06 | 86.95 | 11.98 |
| | 12 | 1.05 | 92.30 | 6.66 |
| | 24 | 1.19 | 96.31 | 2.50 |
| | 26 | 1.23 | 95.97 | 2.80 |
| RD/0013 | 2 | 0.77 | 96.19 | 3.04 |
| | 4 | 0.72 | 99.11 | 0.17 |
| | 6 | 0.73 | 99.12 | 0.15 |
| | 12 | 0.79 | 98.76 | 0.45 |
| | 24 | 0.84 | 99.03 | 0.13 |

(*) Age time at 26 h corresponds to addition of 25% extra formic acid/triethylamine.

Example 7: Preparation of Eslicarbazepine—Effect of the Temperature

The enantioselctive reduction of Oxcarbazepine to Eslicarbazepine has been carried out with the chyral catalysts of the invention, at 60° C., instead of at 75° C. as in experiment 6.

| Conditions | | | | |
|---|---|---|---|---|
| Catalyst eq | DMF vol | Reaction T | Formic acid eq. | Triethylamine eq |
| 0.005 eq | 10 vol | 60° C. | 3.6 eq | 1.4 eq |

| Catalysts | | | | |
|---|---|---|---|---|
| Catalyst | Supplier | CAS # | M.W. | Code name |
| (S,S)-Ts-DENEB | Takasago | 1384974-37-1 | 650.19 | CAT.4 |
| (S,S)-Ms-DENEB | Takasago | 1361318-83-3 | 574.10 | CAT.5 |

Experimental Set-Up

Reaction vessel: 25-mL test tube (EasyMax workstation) with screw cap, septum, magnetic stir bar, temperature probe.

Reaction scale: 1 g of Oxcarbazepine.

Materials: Oxcarbazepine Rixx A1500049.

Raw materials input: all charges are made on physical basis (vs. Oxcarbazepine).

Procedure

Oxcarbazepine (1 g) is charged in the vessel, followed by DMF (5 mL). The mixture is stirred until the solid is uniformly distributed. (S,S)-Ts-DENEB (12.9 mg) (or same molar quantity of (S,S)-MS-DENEB) is added and the catalyst vial is rinsed several time with a total of 5 mL of DMF. A mixture of formic acid (533 μL) and triethylamine (800 μL) is added. The mixture is heated to 60° C. (a clear solution is obtained). The reaction mixture is sampled after 2, 4, 6, 12, 24 h. The solution is analysed by HPLC for conversion and chiral purity.

TABLE 4

Impurity profile of Eslicarbazepine synthesis, chiral IPCs

| | | HPLC LCAP | | |
|---|---|---|---|---|
| Exp # | Age time [h] | R-Licarbazepine RRT 0.59 | Eslicarbazepine RRT 1.00 | Oxcarbazepine RRT 1.09 |
| RD/0013 (S,S)-Ts-DENEB | 2 | 0.77 | 96.19 | 3.04 |
| | 4 | 0.72 | 99.11 | 0.17 |
| | 6 | 0.73 | 99.12 | 0.15 |
| | 12 | 0.79 | 98.76 | 0.45 |
| | 24 | 0.84 | 99.03 | 0.13 |
| RD/0027 (S,S)-Ms-DENEB | 2 | 0.00 | 70.68 | 29.32 |
| | 4 | 0.47 | 88.08 | 11.45 |
| | 6 | 0.55 | 94.07 | 5.38 |
| | 12 | 0.60 | 98.36 | 1.04 |
| | 24 | 0.56 | 99.27 | 0.17 |

Example 8: Preparation of Eslicarbazepine in THF

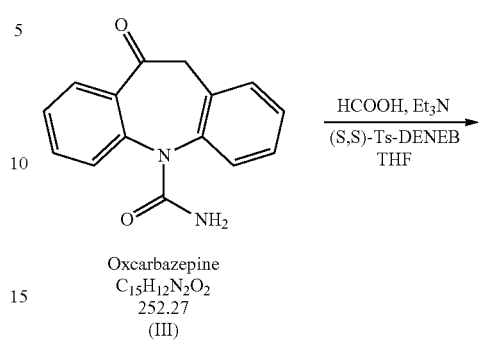

Oxcarbazepine
$C_{15}H_{12}N_2O_2$
252.27
(III)

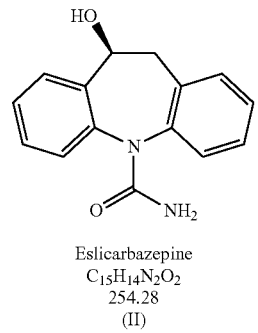

Eslicarbazepine
$C_{15}H_{14}N_2O_2$
254.28
(II)

| Synthetic conditions | | | | | |
|---|---|---|---|---|---|
| Catalyst | Catalyst eq | Solvent | Solvent V | Reaction T | Formic acid eq. | Triethylamine eq |
| (S,S)-Ts-DENEB | 0.005 eq | THF | 10 vol | 60° C. | 3.6 eq | 1.4 eq |

Experimental Set-Up

Reaction vessel: glass vessel (0.1-2 L) equipped with impeller type strirrer.

Reaction scale: 10-150 g of Oxcarbazepine.

Materials: Oxcarbazepine Crude.

Raw materials input: all charges are made on physical basis (vs. Oxcarbazepine).

Procedure

Oxcarbazepine (150 g) is charged in the vessel, followed by THF (1.4 L). The mixture is stirred until the solid is uniformly distributed. (S,S)-Ts-DENEB (1.95 g) is added and the catalyst vial is rinsed several time THF. A mixture of formic acid (80 ml) and triethylamine (120 ml) is added, THF (100 ml) is used as rinsing. The mixture is heated to 60° C. (a clear solution is obtained). The reaction mixture is sampled after a minimum of 12 h. The solution is analyzed by HPLC for conversion and chiral purity. At EoR mixture is cooled to 50° C., charcoal (7.5 g) is charged and mixture stirred at 50° C. for 30 minutes. Following mixture is filtered over dicalite and filter rinsed with pre-heated THF (300 mL). After cooling to T=20/25° C. organic phase is extracted 3 times with saturated NaCl solution (300 mL) then concentrated to final residual volume of 225 ml. MTBE (450 ml) is added and resulting slurry stirred at T=20/25° C., then filtered and cake rinsed with MTBE (225 ml). Product is dried under vacuum at T=40° C. Dry cake analysis for scale up trial (RD-160-1252-0060) are reported in Table 5 below.

TABLE 5

| Exp # | Age time [h] | IPC result Conversion | Eslicarbazepine LCAP | ee % | Dry cake result Yield (mol %) | LCAP | Assay w/w | ee % |
|---|---|---|---|---|---|---|---|---|
| RD/0060 | 17 h | 0.00% | 100.00% | 98.68% | 94.6% | 100% | 90.5% | 98.99% |

Comments

The main outcome and observations of the test are that the conversion rate and the excellent enantioselection and chemical purity were confirmed at scale.

Example 9: Synthesis of Eslicarbazepine Acetate

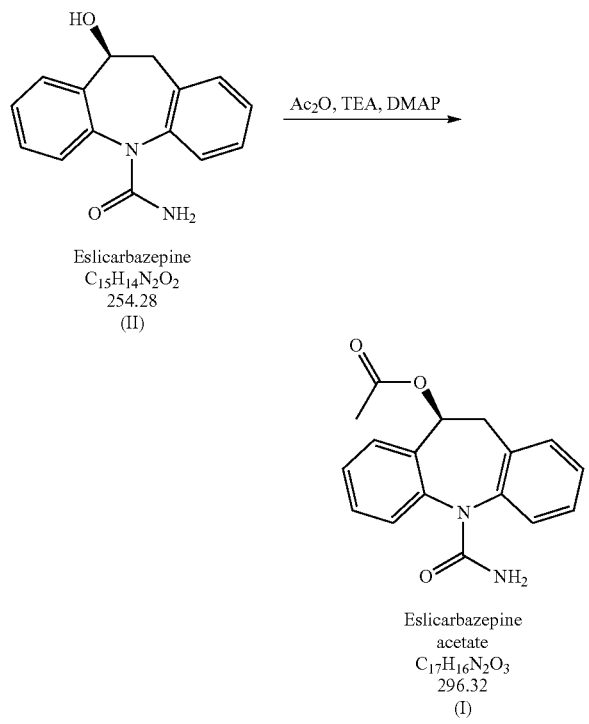

Reaction is performed using acetic anhydride in dichloromethane under catalysis conditions by dimethylaminopyridine (DMAP); triethylamine is used as assistant base.

| Conditions | | | | | |
|---|---|---|---|---|---|
| Catalyst | Catalyst eq | Solvent | Solvent V | Reaction T | Triethylamine eq | Acetic anhydride |
| DMAP | 0.01 eq | DCM | 5 V | 40° C. | 1.2 eq | 1.2 eq |

Experimental Set-Up

Reaction vessel: glass vessel (0.1-2 L) equipped with impeller type stirrer. Raw materials input: all charges are made on physical basis (vs. Eslicarbazepine).

Procedure

Eslicarbazepine (25 g) (as prepared in Example 8) is charged in the vessel, followed by DMAP (0.25 g), dichloromethane (125 ml) and TEA (16.5 ml). The mixture is stirred and cooled to T=5/10° C., then acetic anhydride (12 g) is added dropwise while keeping internal temperature. Reaction mixture is then heated to 40° C. and maintained 2 hours at this temperature, during which dissolution occurs. After HPLC check, mixture is cooled to T=5/10° C. and quenched by addition of a solution made of 19 ml conc. HCl in 100 ml water. After phase separation the organic layer is extracted with a solution of sodium bicarbonate (5 g) in water (100 ml). Finally organic layer is washed with water (100 ml) and concentrated under vacuum to residue. Dichloromethane (25 ml) is charged over the residue followed by ethyl acetate (125 ml). The resulting slurry is stirred at T=40° C. for 15 minutes, then cooled to T=5/10° C. and filtered. Wet cake is rinsed with ethyl acetate (25 ml) and dried under vacuum at T=40° C. for 8 hours. The following Table 6 resumes the experimental results.

TABLE 6

| Exp # | Age time [h] | IPC result Conversion | Eslicarbazepine acetate LCAP | Dry cake result Yield (mol %) | LCAP | Assay w/w | ee % |
|---|---|---|---|---|---|---|---|
| RD/0059 | 2 h | 0.0% | 98.20% | 85.0% | 99.86% | 99.15% | 99.91% |

Example 10: Preparation of Eslicarbazepine

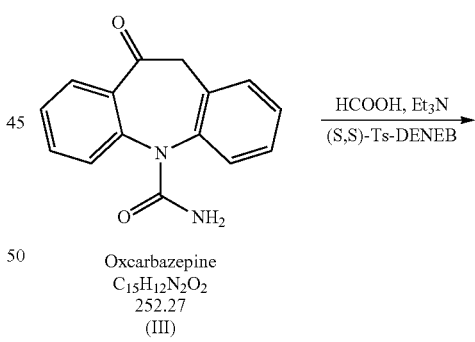

Oxcarbazepine
$C_{15}H_{12}N_2O_2$
252.27
(III)

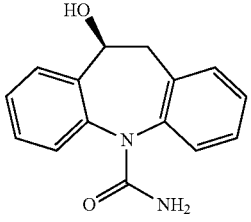

Eslicarbazepine
$C_{15}H_{14}N_2O_2$
254.28
(II)

Material Table

| Material | Amount | FW | Vol/wt Basis (x) |
|---|---|---|---|
| (S,S)-Ts-DENEB | 75.3 mg | 650.2 | 0.05% eq |
| Oxcarbazepine | 58.45 g | 252.27 | 1.0 eq |
| HCOOH | 39.5 g | 46.03 | 3.7 eq |
| Et₃N | 32.8 g | 101.19 | 1.4 eq |
| MeOH | 290 mL | — | 5V |
| Active charcoal | 2.9 g | — | 5% W |
| H₂O | 290 g | — | 5V |

Experimental Procedure

The 500 ml flask equipped with pump automatic controlled by pH meter, condenser, mechanical stirrer and mercury seal, under inert atmosphere (argon).

Charge with 75.3 mg of (S,S)-Ts-DENEB, 58.45 g of Oxcarbazepine, 175 ml of MeOH, stir, then a mixture of HCOOH (14.9 g, 1.4 eq) and Et₃N (32.8 g, 1.4 eq) in MeOH (115 mL) was added through syringe, heated in oil bath (bath temperature 75° C.), when the internal temperature was raised to 50° C., argon was closed. Stirred at reflux, the internal temperature is 60-62° C., pH controlled at pH 6.7-7.2 by added HCOOH automatic (charged additional HCOOH 24.5 g) for about 24 hours, solid dissolution completely, IPC by HPLC, Eslicarbazepine 88.09%, Oxcarbazepine 11.64%.

Stirred for another 14 hours, IPC by HPLC, Eslicarbazepine 99.54%, Oxcarbazepine 0.083%, ee (%) 98.58.

Cool down to 55° C., 2.9 g of activated charcoal was added and kept at 55° C. for 40 minutes. Filter, the filtrate was concentrated under vacuum at 40° C. to a final volume of 2.5V, 290 g of H₂O was added dropwise at 40-45° C., then slowly cold down to about 5° C. and kept 30 minutes. Filter, the wet cake was drying under vacuum at 45° C. overnight, got 50.1 g of Eslicarbazepine, HPLC purity 99.70%, Oxcarbazepine 0.044%, yield 85.0%.

Said procedure has been repeated using acetonitrile as solvent instead of methanol. The in-process control at the end of the reaction shows 0.045% (HPLC NA %) of residual Oxcarbazepine and ee (%) 99.60.

Example 11: Preparation of Eslicarbazepine

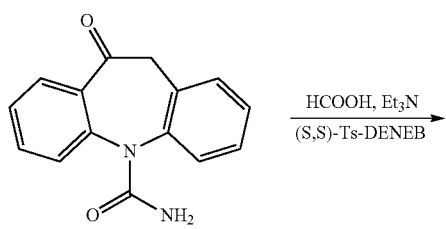

Oxcarbazepine
C₁₅H₁₂N₂O₂
252.27
(III)

$\xrightarrow{\text{HCOOH, Et}_3\text{N}}_{\text{(S,S)-Ts-DENEB}}$

-continued

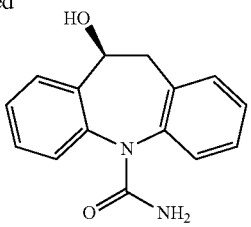

Eslicarbazepine
C₁₅H₁₄N₂O₂
254.28
(II)

In a 100 ml glass vessel, Oxcarbazepine (10 g, 40 mmol) and 50 ml of methanol were charged. Vessel was purged with nitrogen, the suspension was stirred at room temperature for 10 minutes and following triethylamine (1.45 eq, 8 ml, 57 mmol) and formic acid (3.5 eq, 5.3 ml, 140 mmol) were charged. RuCl-(S,S)-Ts-DENEB (0.00075 eq, 19 mg, 0.03 mmol) dissolved in methanol was added under nitrogen atmosphere. The resulting mixture was heated under stirring to reflux temperature for approximately 40 hours, during which additional formic acid was slowly charged to maintain mixture pH at about 5.0. After reaction completion mixture was cooled to 50° C., decolorizing charcoal (0.5 g) was added, stirred for 30 minutes then filtered over dicalite pad; some methanol was used for rinsing. The solution was then concentrated under vacuum to approximately half the initial volume, then 50 ml water were added over approximately 10 minutes. The resulting product slurry was cooled to 5° C., filtered and washed with 15 ml of a methanol/water mixture (1:2). The product was dried under vacuum at 40° C. for 8 hours to afford an off-white powder: 88% isolated yield (8.9 g). HPLC: 99.8% product, 99.2% chiral purity.

Example 12: Preparation of Eslicarbazepine

In a 100 ml glass vessel, Oxcarbazepine (10 g, 40 mmol) and 50 ml of methanol were charged. Vessel was purged with nitrogen, the suspension was stirred at room temperature for 10 minutes and following triethylamine (1.4 eq, 5.6 ml, 56 mmol) and formic acid (2.9 eq, 5.3 g, 116 mmol) were charged. RuCl-(S,S)-Ts DENEB (0.0005 eq, 13 mg, 0.02 mmol) dissolved in methanol was added under nitrogen atmosphere. The resulting mixture was heated under stirring to reflux temperature for approximately 41 hours, during which additional formic acid was slowly charged to maintain mixture pH at about 5.0. After reaction completion mixture was cooled to 50° C., decolorizing charcoal (0.5 g) was added, stirred for 30 minutes then filtered over dicalite pad; some methanol was used for rinsing. The solution was then concentrated under vacuum to approximately half the initial volume, then 50 ml water were added over approximately 10 minutes. The resulting product slurry was cooled to 5° C., filtered and washed with 15 ml of a methanol/water mixture (1:2). The product was dried under vacuum at 40° C. for 8 hours to afford an off-white powder: 86% isolated yield (8.7 g). HPLC: 99.3% product, 99.2% chiral purity.

Example 13: Preparation of Eslicarbazepine

In a 1 L glass vessel, Oxcarbazepine (50 g, 200 mmol) was suspended in 250 ml of methanol. Vessel was purged with nitrogen, the suspension was stirred at room temperature for 10 minutes and triethylamine (1.4 eq, 28.1 g, 280 mmol) was added, followed by formic acid (1.4 eq, 10.4 ml, 280 mmol). RuCl-(S,S)-Ts DENEB (0.0005 eq, 64 mg, 0.1 mmol) dissolved in methanol was added under nitrogen atmosphere. The resulting mixture was heated under stirring to reflux temperature for approximately 36 hours, during which additional formic acid was slowly charged to maintain mixture pH at about 6.2. Upon complete conversion mixture was cooled to 50° C., decolorizing charcoal (0.5 g) was added, stirred for 30 minutes then filtered over dicalite pad; some methanol was used for rinsing. The solution was then concentrated under vacuum to approximately half the initial volume, then 250 ml water were added over approximately 10 minutes. The resulting product slurry was cooled to 5° C., filtered and washed with 75 ml of a methanol/water mixture (1:2). The product was dried under vacuum at 40° C. for 8 hours to afford an off-white powder: 84% isolated yield (42.3 g). HPLC: 99.8% product.

The invention claimed is:

1. A process for the preparation of Eslicarbazepine of formula (II):

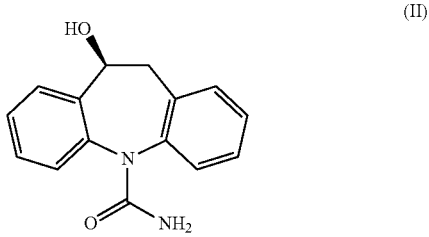 [SMILES: NC(=O)N1c2ccccc2C[C@H](O)c2ccccc21]

(II)

by enantioselective reduction of Oxcarbazepine of formula (III):

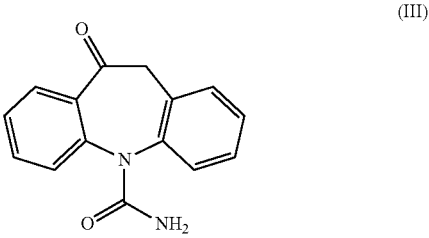 [SMILES: NC(=O)N1c2ccccc2CC(=O)c2ccccc21]

(III)

wherein said enantioselective reduction is carried out in presence a chiral catalyst of formula (IV):

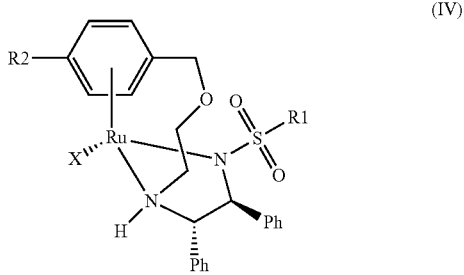

(IV)

wherein X is a hydrogen atom or a halogen atom;
R1 is a linear or branched $C_{1-5}$ alkyl, an unsubstituted aryl, a substituted aryl with a linear or branched $C_{1-5}$ alkyl group or is a linear or branched $C_{1-5}$ alkyl-aryl; and R2 is hydrogen, a linear or branched $C_{1-5}$ alkyl, linear or branched $C_{1-5}$ alkoxy group.

2. The process according to the claim 1, wherein X is chlorine and R2 is methyl.

3. The process according to claim 1, wherein R1 is methyl or tosyl.

4. The process according to claim 1, wherein the chiral catalyst of formula (IV) has the following structure:

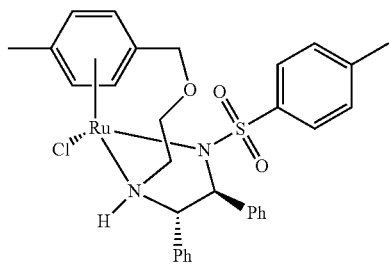

or the chiral catalyst has the following structure:

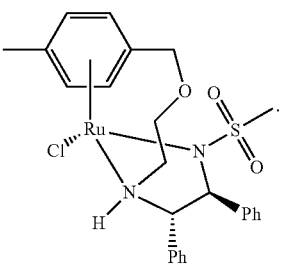

5. The process according to claim 1, wherein the molar ratio of the chiral Ruthenium catalyst of formula (IV) to Oxcarbazepine of formula (III) is from 1:200 to 1:1000.

6. The process according to claim 1, wherein the molar ratio of the chiral Ruthenium catalyst of formula (IV) to Oxcarbazepine of formula (III) is from 1:1430 to 1:3330.

7. The process according to claim 1, wherein the enantioselective reduction is an asymmetric transfer hydrogenation.

8. The process according to the claim 7, wherein the hydride source is formic acid and triethylamine or is diazabicyclo[2.2.2]octane and triethylamine.

9. The process according to claim 1, wherein enantioselective reduction is carried out in methanol or THF as solvent.

10. The process according to claim 1, wherein enantioselective reduction is carried out at a temperature of between 50° C. and 80° C.

11. The process according to claim 1, further comprising the step of conversion of Eslicarbazepine of formula (II) to give Eslicarbazepine acetate of formula (I).

12. A process for the preparation of Eslicarbazepine acetate of formula (I):

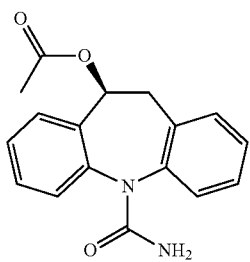

comprising:

A) preparing Eslicarbazepine of formula (II):

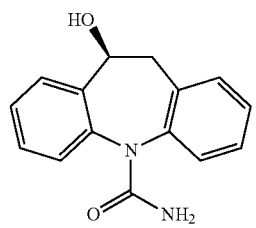

according to the process of claim 1; and
B) converting the Eslicarbazepine of formula (II) as prepared in step A to give Eslicarbazepine acetate of formula (I).

13. The process according to claim 11, wherein the conversion of Eslicarbazepine of formula (II) to give Eslicarbazepine acetate of formula (I) is carried out by an acetylation reaction.

14. The process according to the claim 13, wherein Eslicarbazepine of formula (II) is isolated and then acetylated to produce Eslicarbazepine acetate of formula (I).

* * * * *